(12) United States Patent
Klausen (10) Patent No.: US 10,076,430 B2
(45) Date of Patent: Sep. 18, 2018

(54) DEVCE WITH TENSIONERS

(71) Applicant: Cook Medical Technologies LLC, Bloomington, IN (US)

(72) Inventor: Kasper Klausen, Lille Skensved (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 58 days.

(21) Appl. No.: 15/291,384

(22) Filed: Oct. 12, 2016

(65) Prior Publication Data

US 2017/0105855 A1   Apr. 20, 2017

Related U.S. Application Data

(60) Provisional application No. 62/243,284, filed on Oct. 19, 2015.

(51) Int. Cl.
 *A61F 2/82* (2013.01)
 *A61F 2/89* (2013.01)
 *A61F 2/95* (2013.01)

(52) U.S. Cl.
 CPC .............. *A61F 2/89* (2013.01); *A61F 2/95* (2013.01); *A61F 2230/0069* (2013.01); *A61F 2230/0073* (2013.01)

(58) Field of Classification Search
 CPC ...... A61F 2/06; A61F 2/82; A61F 2/92; A61F 2/89; A61F 2/95
 USPC ................................................ 623/1.15–1.48
 See application file for complete search history.

(56) References Cited

U.S. PATENT DOCUMENTS

| | | | | |
|---|---|---|---|---|
| 5,360,440 A | * | 11/1994 | Andersen | A61N 1/05 607/115 |
| 6,221,096 B1 | * | 4/2001 | Aiba | A61F 2/86 606/108 |
| 6,436,132 B1 | * | 8/2002 | Patel | A61F 2/07 623/1.13 |
| 6,663,664 B1 | | 12/2003 | Pacetti | |
| 7,011,678 B2 | * | 3/2006 | Tenerz | A61F 2/91 623/1.15 |
| 7,435,255 B1 | * | 10/2008 | Rao | A61F 2/92 623/1.13 |
| 8,663,314 B2 | * | 3/2014 | Wood | A61F 2/90 623/1.15 |
| 2001/0032009 A1 | * | 10/2001 | Layne | A61F 2/07 623/1.13 |
| 2002/0038146 A1 | * | 3/2002 | Harry | A61F 2/91 623/1.16 |
| 2007/0073383 A1 | * | 3/2007 | Yip | A61F 2/90 623/1.16 |

(Continued)

FOREIGN PATENT DOCUMENTS

WO   WO 2014091438   6/2014

*Primary Examiner* — Suzette J Gherbi
(74) *Attorney, Agent, or Firm* — Brinks Gilson & Lione (57) ABSTRACT

This disclosure provides for a medical device to be implanted in the vasculature and a method for treatment in the vasculature. The device has an outer layer of a first material and an inner layer of a second material attached to the outer layer. The inner layer further has a plurality of elastomeric tensioners. If the device experiences relaxation, resulting in a decreased radial force against the vessel wall, the elastomeric tensioners may provide a contraction force to the inner layer and the outer layer, resulting in a maintained radial force on the vessel wall.

15 Claims, 6 Drawing Sheets

(56) References Cited

U.S. PATENT DOCUMENTS

| | | | |
|---|---|---|---|
| 2007/0293930 A1 | 12/2007 | Wang et al. | |
| 2008/0154351 A1 | 6/2008 | Leewood et al. | |
| 2009/0312834 A1* | 12/2009 | Wood | A61F 2/90 623/1.44 |
| 2011/0125254 A1* | 5/2011 | Kang | A61F 2/90 623/1.42 |
| 2012/0310327 A1* | 12/2012 | McHugo | A61F 2/90 623/1.15 |
| 2013/0060327 A1* | 3/2013 | Shokoohi | A61F 2/856 623/1.42 |
| 2014/0180392 A1* | 6/2014 | Shoham | A61F 2/852 623/1.15 |
| 2014/0207176 A1 | 7/2014 | Gilson et al. | |
| 2014/0277391 A1* | 9/2014 | Layman | A61F 2/915 623/1.32 |
| 2014/0288634 A1* | 9/2014 | Shalev | A61F 2/852 623/1.16 |
| 2015/0216684 A1* | 8/2015 | Enzmann | A61F 2/07 623/1.36 |
| 2016/0022448 A1* | 1/2016 | Tobis | A61F 2/848 623/1.16 |
| 2017/0035548 A1* | 2/2017 | Bebb | A61F 2/07 |
| 2017/0216062 A1* | 8/2017 | Armstrong | A61F 2/07 |
| 2017/0265870 A1* | 9/2017 | Kealey | A61B 17/12118 |

* cited by examiner

DEVCE WITH TENSIONERS

CROSS-REFERENCE TO RELATED APPLICATIONS

This application claims the benefit of priority under 35 U.S.C. § 119(a) to U.S. Provisional Application No. 62/243,284, filed Oct. 19, 2015 all of which are hereby incorporated by reference in their entirety.

BACKGROUND

1. Technical Field Text

The present disclosure relates to medical devices. More particularly, the disclosure relates to a bioabsorbable device and method of treatment with the device.

2. Background Information

Often, physicians use vascular implantable devices to treat various conditions. Such devices may be designed to exert a radial force against a vein or body vessel having a vessel wall. In some cases, the vessel wall may be highly flexible. It may be advantageous for the device to accommodate the natural environmental forces experienced by the vessel wall, while maintaining treatment capacity and vessel patency. For example, a vena cava filter may be used to treat pulmonary embolism and thrombosis.

Over time the device may experience relaxation or deformation, which results in a decreased radial force against the vessel wall. This may result in unintended migration of the device in the body vessel. In this case, it may be desirable to have a device that can maintain the radial force against the vessel wall to avoid unintended migration.

After the device serves its intended purpose, the user may desire to remove the device. However, a secondary procedure to remove the device may result in unintended consequences. In some cases, it may be advantageous to have a device that can maintain the radial force against the vessel wall during use and then be partially or completely removable when the intended use terminates.

BRIEF SUMMARY

The present disclosure provides generally for a bioabsorbable implantable device. The disclosure also provides generally for a method of treatment using said device. The device may be implanted in a body vessel with a vessel wall. The device may have a longitudinal axis that may run along the vessel's longitudinal axis. Generally, the device may have an outer layer, inner layer, and plurality of elastic tensioners.

The outer layer may be formed from a first material with a plurality of outer cells. The plurality of outer cells may be arranged in outer circumferential rows with each outer cell having an outer perimeter. Each outer perimeter may have a first outer cell edge attached to a second outer cell edge at a distal outer cell end, defining a distal outer angle, and a third outer cell edge attached to a fourth outer cell edge at a proximal outer cell end, defining a proximal outer angle. The distal outer angle may be distal the proximal outer angle along the longitudinal axis.

The inner layer may be formed from a second material being elastic or elastomeric. The inner layer may also contain a plurality of inner cells. The plurality of inner cells may be arranged in inner circumferential rows with each inner cell having an inner perimeter. The outer and inner layers may define a tubular body having a proximal end extending to a distal end and a lumen formed therethrough, the tubular body being movable between a collapsed state for delivery and an expanded state for treatment in the body vessel. The inner perimeter may have a first inner cell edge attached to a second inner cell edge at a distal inner cell end, defining a distal inner angle in the expanded state, and a third inner cell edge attached to a fourth inner cell edge at a proximal inner cell end, defining a proximal inner angle in the expanded state. The distal inner angle may be distal the proximal inner angle along the longitudinal axis. At least one outer perimeter may be attached to at least one inner perimeter.

The plurality of tensioners may have an extended length and a contracted length. The tensioners may be made of the second material with each inner cell having one tensioner. Further, one tensioner may be attached to the proximal inner cell end and may extend distally to the distal inner cell end to apply a contraction force on the one inner cell.

One tensioner may form a first angle with the first inner cell edge and a second angle with the second inner cell edge, the sum of the first and second angles may be about the same as the distal inner angle. The first and second angles may be between about 25 to about 50 degrees each in the expanded state.

The outer and inner layers may define a tubular body having a proximal end extending to a distal end and a lumen formed therethrough. The tubular body may have a collapsed state for delivery and an expanded state for treatment in the body vessel. The tubular body is movable between the expanded state and the collapsed state.

In the expanded state, the tensioners may have an extended length and a contracted length to maintain a radial force on the vessel wall. For example, the outer layer or tubular body lengthens or experiences a lengthening force and the tensioners counter the lengthening force with the contraction force to move from an extended length to a contracted length to maintain a radial force on the vessel wall.

The second and third outer cell edges may form a first outer cell apex and the first and fourth outer cell edges may form a second outer cell apex. The second and third inner cell edges may form a first inner cell apex and the first and fourth inner cell edges may form a second inner cell apex. In one embodiment, the outer and inner perimeters may be rhombic. In another embodiment, the first and second outer cell apices and the first and second inner cell apices are arcuate. Likewise, the first outer and inner cell apices are each about 80 degrees to about 130 degrees in the expanded state and the second outer and inner cell apices are each about 80 degrees to about 130 degrees in the expanded state.

The inner layer, outer layer, and tensioner may be a co-extrusion of the first and second materials. In addition, the first material may be a high mechanical strength material. The high mechanical strength material may be a material selected from the group consisting of a polyurethane, a polyester, a polyanhydride, a polylactide, poly-L-lactic acid, poly-L/D-lactic acid, and a co-polymer of poly lactic-co-glycolic acid and polycaprolactone. The elastomeric second material may contain polycaprolactone, the polycaprolactone content ranging from about 10 percent to about 100 percent of the elastomeric material. In one embodiment, the first and second materials may be biodegradable.

The device in any embodiment may further contain a plurality of filter struts attached to the inner layer. In another embodiment, the device may contain a plurality of filter struts attached to the outer layer. In another embodiment, the device may contain a plurality of filter struts attached to each of the inner layer and the outer layer. Each filter strut may contain a proximal segment attached to the distal end and extending distally to a distal segment wherein all distal segments are attached to each other, gathered at a center point along the longitudinal axis. The plurality of filter struts may be about six to about twelve filter struts. The tubular body may have a length of about 25 millimeters to about 60 millimeters between the proximal and distal ends.

As one advantage to the device discussed herein, having an outer and inner layer allows the use of two different materials in the tubular body. For example, if the first material is susceptible to relaxation, the inner layer may comprise a second material to aid in maintaining the radial force against the vessel wall. This advantage may be particularly useful with biodegradable materials as the first material. In addition, this advantage may be particularly useful within the vena cava, which is highly flexible and may experience normal physiological or mechanical forces that act on or by the device.

This disclosure also provides a method of treatment in the body vessel with the device discussed herein. The method includes disposing the device within the body vessel; lengthening by a lengthening force on the outer layer or tubular body; and countering the lengthening force by a contraction force with the plurality of tensioners to maintain the outer layer or tubular body in the radial direction. The method may further comprise allowing the device to biodegrade after the step of countering.

The step of lengthening by a lengthening force may comprise the lengthening force being perpendicular to the longitudinal axis. The step of countering the lengthening force may comprise countering with a first contraction force in a first direction and a second contraction force in a second direction, the first and second directions being along the longitudinal axis.

Further objects, features, and advantages of the invention will become apparent from consideration of the following description and the appended claims when taken in connection with the accompanied drawings.

DETAILED DESCRIPTION

The present disclosure provides for a bioabsorbable implantable device for treatment in a vein or body vessel. The disclosure also provides for a method of treatment with the device. The materials, methods, and examples disclosed are illustrative only and not intended to be limiting. The disclosed figures are not necessarily drawn to scale.

All publications, patent applications, patents, and other references mentioned herein are incorporated by reference in their entirety. Unless otherwise defined, all technical and scientific terms used herein have the same meaning as commonly understood by on of ordinary skill in the art to which this disclosure pertains. In case of conflict, the present document and definition will control.

"Adjacent" referred to herein is near, near to, or in close proximity with.

"Longitudinally" and derivatives thereof will be understood to mean along the longitudinal axis of the device.

"Mechanical strength" referred to herein is the stiffness and strength of a material. Mechanical strength may be measured in the circumferential, radial, or longitudinal direction of the device.

The terms "proximal" and "distal" and derivatives thereof will be understood in the frame of reference of a physician using the device. Thus, proximal refers to locations closer to the physician and distal refers to the locations farther away from the physician (e.g., deeper in the patient's vasculature).

"Radially" and derivatives thereof will be understood to mean along a radial axis of the body vessel. Likewise, "radial force" and derivatives thereof will be understood to mean a force applied along the radial axis.

Figure 1A:
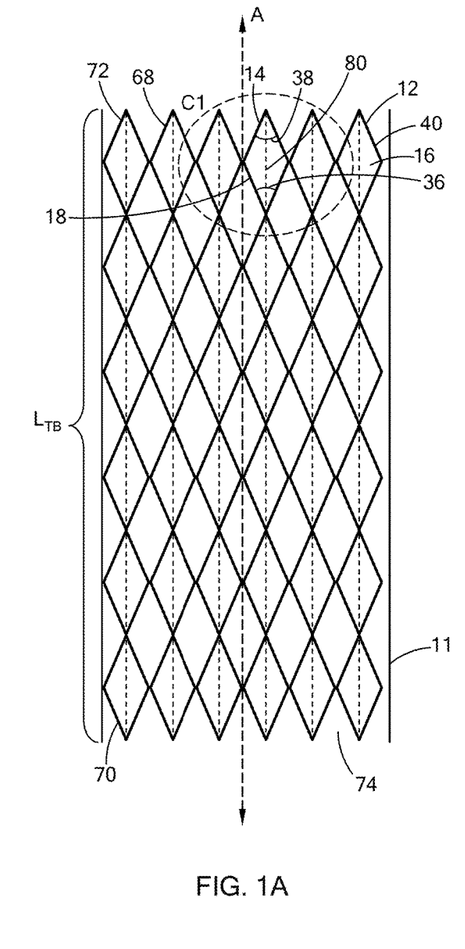
FIG. 1A is a an environmental side view of a medical device for treatment in a body vessel in accordance with one embodiment of the present invention.
Figure 1B:
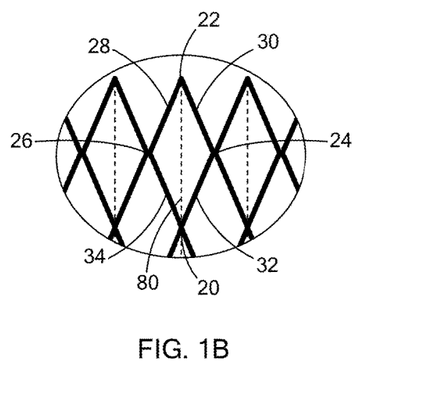
FIG. 1B is a blown-up partial view of the device of FIG. 1A in circle $C_1$.
Figure 2A:
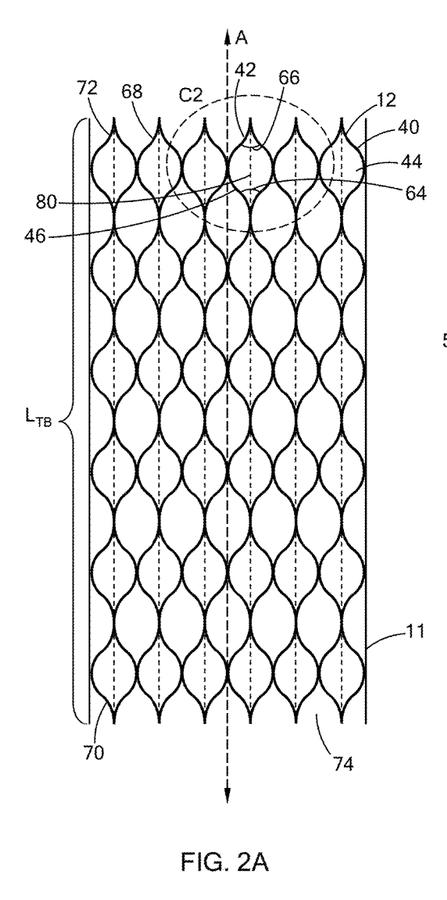
FIG. 2A is an environmental side view of the device in accordance with another embodiment of the present invention.
Figure 2B:
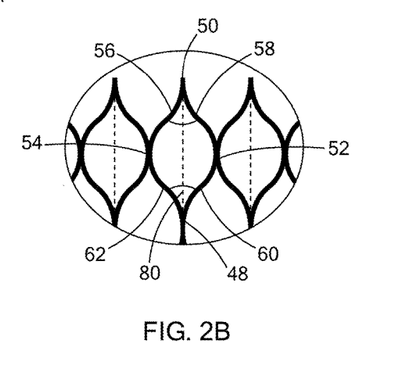
FIG. 2B is a blown-up partial view of the device in FIG. 2A in circle $C_2$.

FIGS. 1 and 2 depict two embodiments of the medical device discussed herein. The device may be disposed in a body vessel having a vessel wall 11. The device also has a longitudinal axis A. In FIG. 1A, the device has an outer layer 12 comprising a first material and a plurality of outer cells 14. The plurality of outer cells 14 are arranged in outer circumferential rows 16 with each outer cell 14 having an outer perimeter 18.

FIG. 1B depicts the details of the outer perimeter 18. FIG. 1B is a blown-up view of FIG. 1A around circle $C_1$. Each outer perimeter 18 may have a first outer cell edge 28 attached to a second outer cell edge 30 at a proximal outer cell end 22. The first outer cell edge 28 and the second outer cell edge 30 define a distal outer angle 38. The outer perimeter 18 also may have a third outer cell edge 32 attached to a fourth outer cell edge 34 at a proximal outer cell end 20. The third outer cell edge 32 and the fourth outer cell edge 34 make a proximal outer angle 36. The distal outer angle 38 is distal the proximal outer angle 36 along axis A.

Although FIGS. 1A-B do not depict details of the inner layer, it will be understood that the inner layer may be obscured by the outer layer 12 in the two-dimensional views in FIGS. 1A-B. In FIGS. 2A-B, details of the inner layer are depicted. It will be understood that the outer layer may normally obscure the inner layer in some views. The device also comprises an inner layer 40 having a second material being elastomeric and a plurality of inner cells 42. The plurality of inner cells 42 are also arranged in inner circumferential rows 44, with each inner cell 42 having an inner perimeter 46.

As with FIG. 1B, FIG. 2B depicts the details of the inner perimeter 46. In FIG. 2B, the inner perimeter 46 has a first inner cell edge 56 attached to a second inner cell edge 58 at a distal inner cell end 50. The first inner cell edge 56 and the second inner cell edge 58 define a distal inner angle 66. The inner perimeter 46 further has a third distal cell edge 60 attached to a fourth distal cell edge 62 at a proximal inner cell end 48. The third inner cell edge 60 and the fourth inner cell edge 62 define a proximal inner angle 64. The distal inner angle 66 is distal the proximal inner angle 64 along the longitudinal axis A.

In one embodiment, the distal outer angle 38 and the proximal outer angle 36 may be between about 50 to about 100 degrees. Likewise, the distal inner angle 66 and the proximal inner angle 64 may be between about 50 to about 100 degrees.

It will be understood that although FIGS. 1 and 2 depict features of the outer and inner layers, respectively, each embodiment may contain both an outer and inner layer. Details of both layers are not shown in each figure for the sake of clarity. Further, at least one outer perimeter 18 is attached to at least one inner perimeter 46. There may be about two to about eight outer circumferential rows 16 in the outer layer 12 and inner circumferential rows 44 in the inner layer 40 in the longitudinal direction. FIGS. 1A and 2A depict six circumferential rows each.

Figure 7A:
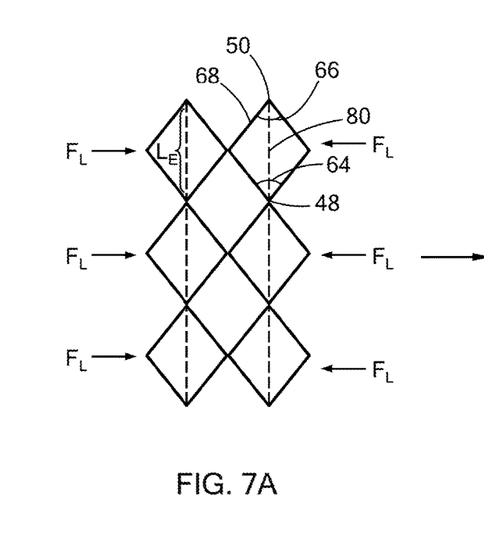
FIGS. 7A-B depicts steps of the method in FIG. 6.
Figure 7B:
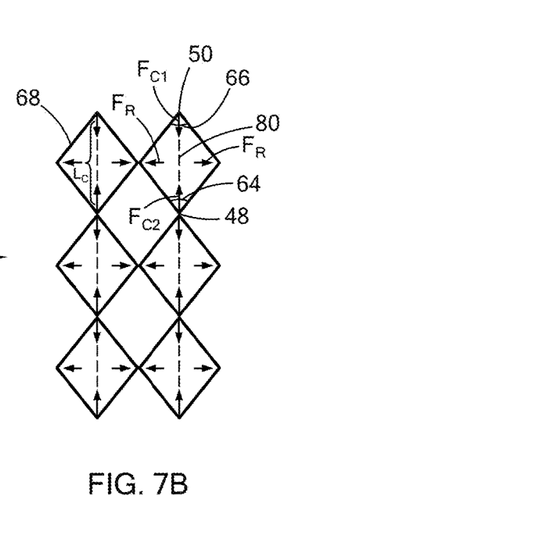

In FIGS. 1-2, the device comprises a plurality of tensioners 80 having an extended length and a contracted length (discussed in further detail in FIG. 7). The plurality of tensioners 80 may be formed from the second material. In addition, each tensioner may be a filament, tubing, or braided thread.

Each tensioner 80 is disposed within one inner cell 42, being attached to the proximal inner cell end 48 and extending distally to the distal inner cell end 50 to apply a contraction force on at least one inner cell 42. In one embodiment, each inner cell 42 has one tensioner 80 being attached to the proximal inner cell end 48 and extending distally to the distal inner cell end 50, although other distributions of the tensioners are possible.

The outer layer 12 and inner layer 40 may define a tubular body 68 having a proximal end 70 extending to a distal end 72, and a lumen 74 formed therethrough. The tubular body 68 has a length $L_{TB}$. The tubular body 68 comprises a collapsed state for delivery and an expanded state for treatment in the body vessel. In the expanded state (FIGS. 1-2), the outer layer 12 may experience or receive a lengthening force and the tensioners 80 counter the lengthening force with a contraction force to move from an extended length to a contracted length to maintain a radial force on the vessel wall.

As shown in FIG. 1 B, the second and third outer cell edges (30 and 32, respectively) form a first outer cell apex 24. Additionally, the first and fourth outer cell edges (28 and 34, respectively) form a second outer cell apex 26. Correspondingly in FIG. 2B, the second and third inner cell edges (58 and 60, respectively) form a first inner cell apex 52 and the first and fourth inner cell edges (56 and 62, respectively) form a second inner cell apex 54. Likewise, first outer and inner cell apices are each about 80 degrees to about 130 degrees in the expanded state and the second outer and inner cell apices are each about 80 degrees to about 130 degrees in the expanded state.

In FIGS. 1A-B, the outer and inner perimeters (18 and 46, respectively) are rhombic. Each cell has a rhombic shape. In FIGS. 2A-B, the first and second outer cell apices and the first and second inner cell apices (52 and 54, respectively) are arcuate.

Figure 3A:
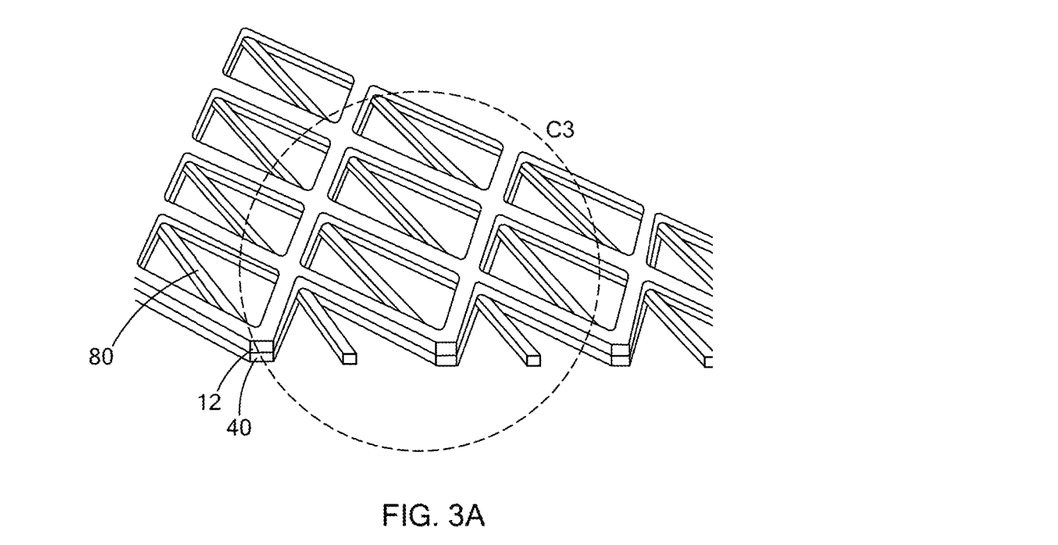
FIG. 3A is a three-dimensional side view of the device in FIG. 1A.

FIG. 3A shows a detailed view of the outer and inner layers (12 and 40, respectively). In one embodiment, outer layer 12, the inner layer 40, and the tensioners 80 are co-extruded. In this embodiment, the first material and the second material are co-extruded to form the tubular body. As a co-extrusion, the first and second materials may be formed together, attached. In this case, the first material of the outer layer 12 may be removed as necessary to expose the second material of the inner layer 40. This removal could be done through any technique known in the art, including ablating the outer layer.

Ablation is a technique where a portion of material is removed by vaporization, chipping, or melting to expose another portion of material. This technique may be used to remove any portion of material discussed in this disclosure, including excess or unnecessary material during manufacturing.

Alternatively, the outer and inner layers may be formed separately. Such layers could be attached at a later time or as a secondary step via any method known in the art. Some examples include bonding, gluing, welding, or other similar methods to attach the outer and inner layers.

Figure 3B:
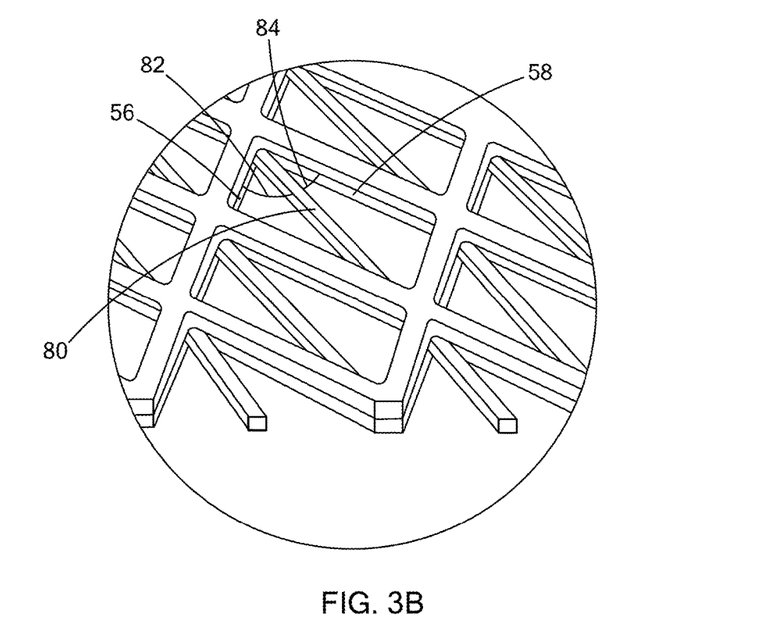
FIG. 3B is a partial side view of the device in FIG. 3A in circle $C_3$.

As shown in the blown-up partial view depicted in FIG. 3B around circle $C_3$, tensioner 80 forms a first angle 82 with the first inner cell edge 56 and a second angle 84 with the second inner cell edge 58. The sum of the first and second angles (82 and 84, respectively) is about the same as the distal inner angle. In one embodiment, the first and second angles (82 and 84, respectively) are between about 25 to degrees about 50 degrees in the expanded state.

The device may be formed from whatever first and second materials suit the intended application. In one embodiment, the first material differs from the second material such that both materials contribute different properties to the device (e.g. mechanical strength). For example, the first material may be a high mechanical strength material. Such high mechanical strength material may provide strength and stiffness in the circumferential, radial, or longitudinal directions during treatment. The high mechanical strength material may be a material selected from the group consisting of poly-L-lactide, poly-L-lactic acid, poly-D/L-lactic acid, and a co-polymer of poly lactic-co-glycolic acid and polycaprolactone. In one aspect, the high mechanical strength material is 100% poly-L-lactide.

Additionally, the second material may be elastomeric to provide a contraction force on the first material and the device. For example, the elastomeric material may form the tensioners and apply the contraction force on the inner layer at the points where the tensioners connect with the inner layer. In turn, this applies a force on the outer layer. The elastomeric material may be polycaprolactone and range from about 100% polycaprolactone to about 10% polycaprolactone, wherein the polycaprolactone may be a copolymer with another material. In one aspect, the elastomeric material is about 50% polycaprolactone.

In one embodiment, the first and second materials are both biodegradable. In this embodiment, over time the entire device will biodegrade within the body and will require no secondary removal procedure. One skilled in the art will understand that the device could also be partially biodegradable, wherein either the first or second materials may be biodegradable.

Figure 4A:
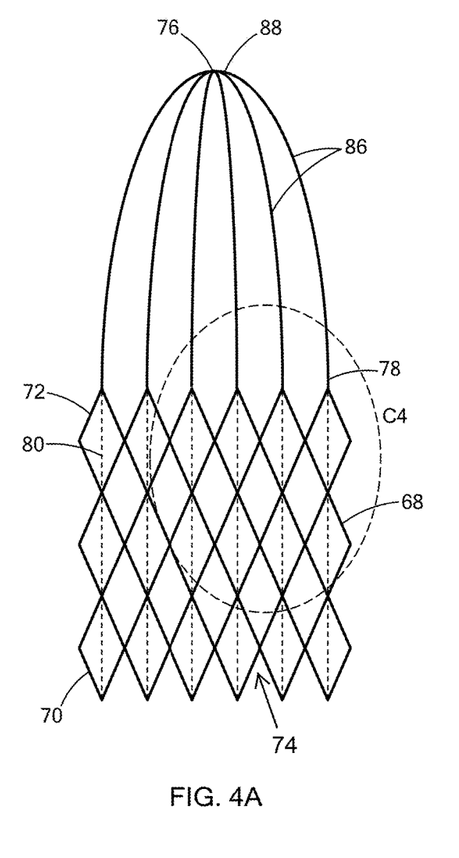
FIG. 4A is a partial side view of the device in accordance with another embodiment of the present invention.
Figure 4B:
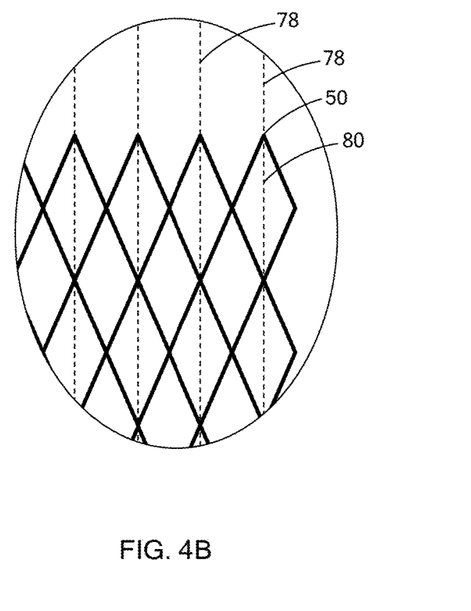
FIG. 4B is a blown-up partial view of the device in FIG. 4A in circle $C_4$.

In an additional embodiment as shown in FIG. 4A-B, the device may have a plurality of filter struts 86 attached to the inner layer. As in FIG. 4A, each filter strut 86 may have a proximal segment 78 attached to the distal end 72 and extend distally to a distal segment 88 wherein all distal segments 88 are gathered at a center point 76 along the longitudinal axis.

The distal segments 88 may be directed attached to each other at the center 76. They could also be attached to each other at other points.

FIG. 4B shows a blown-up view of the attachment of the proximal segment 78 to the inner layer in circle $C_4$. Each proximal segment 78 may extend directly from one tensioner 80 at the distal inner cell end 50. Alternatively or additionally, the plurality of filter struts 86 may attach between the proximal and distal ends (70 and 72, respectively). For example, the filter struts 86 may have a similar configuration as shown in FIG. 4A, but extend within the lumen 74. There may be more than one set of filter struts throughout the device. For example, there may be one set at the proximal end and one set at the distal end.

The device may have a plurality of filter struts 86 from about six to about 12 filter struts. The filter struts 86 may be formed from any suitable material, including the first material or the second material. The filter struts may be co-extruded with the tubular body or, alternatively, attached to the tubular body by any means known in the art.

The dimensions of the entire device could be changed to fit the intended body vessel. For example, the tubular body may have a length $L_{TB}$ of about 25 millimeters to about 85 millimeters, or about 25 millimeters to about 60 millimeters between the proximal and distal ends (70 and 72, respectively). In the event that filter struts are present, the filter struts 86 could be about 25 millimeters to about 60 millimeters each in length as well.

Further, in the event that filter struts are attached to the distal end 72, the length of the tubular body and the filter strut 86 could be about 30 millimeters each, resulting in a total length of about 60 millimeters. The diameter of the tubular body would be about 35 millimeters in the expanded state. Correspondingly, the diameter of the tubular body could be about 5 millimeters in the collapsed state, crimped or compressed.

Figure 5A:
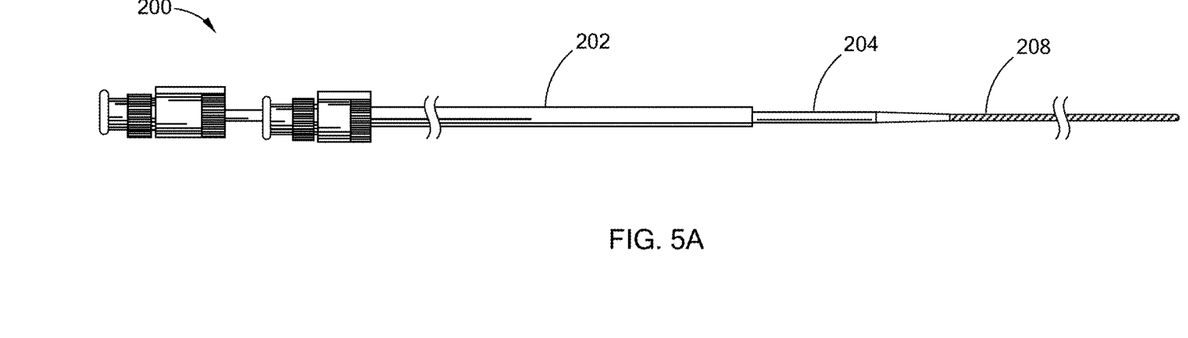
FIGS. 5A-B are a delivery assembly for introducing the device in any embodiment of the present invention discussed herein.
Figure 5B:
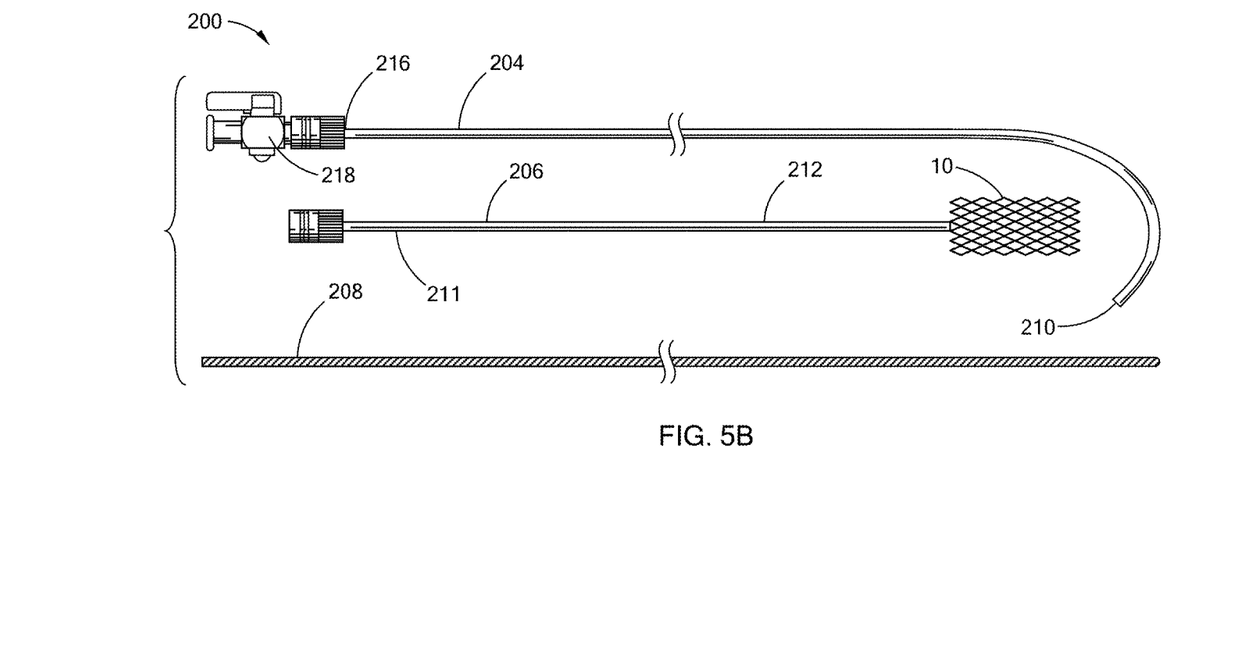

FIGS. 5A-B depict a delivery assembly for delivering the device 10. The device 10 may be delivered or retrieved by way of the Seldinger technique. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner member or catheter 206 to be percutaneously inserted to a desired location in the body vessel. The inner member may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device 10 may also be used to expand the access site.

When the distal end 210 of the outer sheath 204 is at the desired location in the body vessel, the wire guide 208 is removed and the device 10, having a proximal segment contacting a distal portion 212 of the inner catheter 206, is inserted into the outer sheath 204. The inner catheter 206 is advanced through the outer sheath 204 for deployment of the device 10 through the distal end 210 to treat the body vessel. The catheter 206 extends from a proximal portion 211 to a distal portion 212 and is configured for axial movement relative to the outer sheath 204.

In this example, the distal portion 212 is shown adjacent to the device. Thus, before deployment, the device 10 is coaxially disposed within the lumen of the outer sheath 204 and removably coupled to the distal portion 212 of the catheter 206, or in the alternative, the device 10 is merely pushed by, but not coupled to, the distal portion 212 of the catheter 206.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner catheter 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end 210 of the outer sheath 204 adjacent the deployed device in the vasculature. The inner catheter 206 is advanced through the outer sheath 204 until the distal portion 212 protrudes from the distal end 210 of the outer sheath 204. The distal portion 212 is coupled to a proximal end of the device 10, after which the inner catheter 206 is retracted proximally, drawing the device 10 into the outer sheath 204.

The device 10 has a collapsed state for delivery and an expanded state for filtering once delivered to the desired location in the body vessel. In the collapsed state, the device 10 is disposed inside the delivery assembly. The device 10 may be self-expanding or expandable to the expanded state upon exiting the delivery assembly for filtering (as shown in FIG. 5B).

The assembly described above is merely one example of an assembly that may be used to deploy the device in a body vessel. Of course, other apparatus, assemblies and systems may be used to deploy any embodiment of the device without falling beyond the scope or spirit of the present invention.

Figure 6:
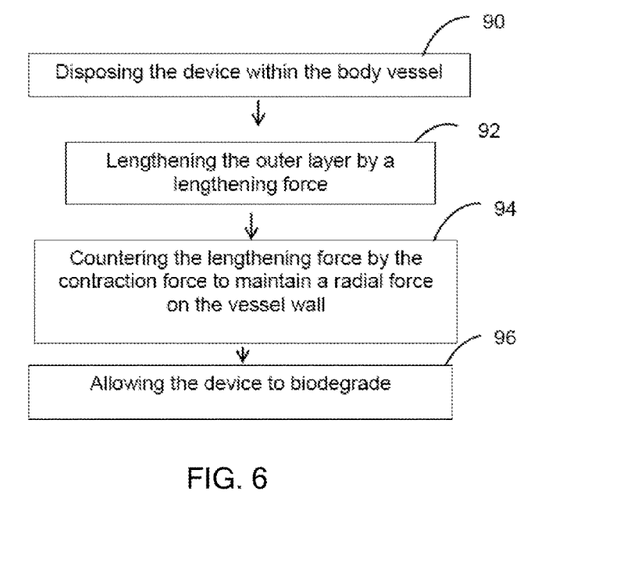
FIG. 6 is a flow diagram of one embodiment of treatment in the vessel with the device in any embodiment in accordance with the present invention.

FIG. 6 shows a flow diagram of the steps of one method to treat the body vessel using the device. In step 90, the device may be disposed within the body vessel. The device may have any or all of the features discussed herein. In step 92, the device may lengthen by a lengthening force on the outer layer or tubular body. In step 94, the device may counter the lengthening force with a contraction force from the plurality of tensioner to expand the outer layer or tubular body in the radial direction. If the device contains biodegradable material, in step 96, the device may biodegrade.

FIGS. 7A-B depict the steps of the method in FIG. 6. In FIG. 7A, the device may lengthen by a lengthening force $F_L$ on the tubular body 68. This lengthening force $F_L$ may be an internal force of the device or an external force on the device as a result of natural physiology. This lengthening force $F_L$ may causes the outer layer to deform or relax and increase the length of the elastomeric tensioners 80 from a default position to an expanded length $L_E$. This relaxation may cause the proximal and distal angles to decrease (64 and 66, respectively).

As a result in FIG. 7B, the tensioners 80 may apply a contraction force on the inner layer of the tubular body 68. For example, the contraction force may be a first contraction force $F_{C1}$ in a first direction and a second contraction force $F_2$ in a second direction. The first and second directions may be opposite from each other and along the longitudinal axis. This contraction force may decrease the length of the tensioners 80 from the expanded length $L_E$ to a contracted length $L_C$.

The expanded and contracted lengths of the tensioners may not be the longest and shortest lengths, respectively, that the tensioners may have. For example, the device may have a relaxed stated, where it is not disposed within a body vessel and has no external forces acting on it. In this relaxed state, the tensioners may naturally assume their shortest length. Contrastingly, the device may have a crimped or delivery state where the device has a small diameter. In this state, the tensioners may assume their longest length. Instead, the expanded and contracted lengths of the tensioners refer to those lengths when the device is implanted within a body vessel. Thus, these particular lengths should be understood in reference to each other and not to an absolute longest or shortest length possible for the tensioners.

This contraction force may also increase the magnitude of the proximal and distal inner angles (64 and 66, respectively). Correspondingly, this may increase the magnitude of the proximal and distal outer angles (48 and 50, respectively). Finally, the contraction forces may result in an increased radial force $F_R$ on the vessel wall, which maintains the outward tension of the device on the vessel wall. The radial force $F_R$ may result from a circumferential force of each cell, as shown in FIG. 7B. Even if the materials are biodegradable, the tensioners 80 may assist in maintaining an outward radial force against the vessel wall. The contraction forces may act on the tubular body until at least the time that the device is embedded into the vessel wall tissue through endothelialization. Over time, part or all of the device may degrade and be absorbed.

While the present invention has been described in terms of certain embodiments, it will be understood that the invention is not limited to these disclosed embodiments and those having skill in the art may make various modifications without departing from the scope and purpose of the following claims.

The invention claimed is:

1. A medical device for treatment in a body vessel having a vessel wall, the device having a longitudinal axis and comprising:

an outer layer comprising a first material and a plurality of outer cells arranged in outer circumferential rows, each outer cell having an outer perimeter comprising a first outer cell edge attached to a second outer cell edge at a distal outer cell end, defining a distal outer angle, and a third outer cell edge attached to a fourth outer cell edge at a proximal outer cell end, defining a proximal outer angle, the distal outer angle being distal the proximal outer angle along the longitudinal axis;

an inner layer comprising a second material being elastomeric and a plurality of inner cells arranged in inner circumferential rows, the outer and inner layers defining a tubular body having a proximal end extending to a distal end and a lumen formed therethrough, the tubular body being movable between a collapsed state for delivery and an expanded state for treatment in the body vessel, each inner cell having an inner perimeter comprising a first inner cell edge attached to a second inner cell edge at a distal inner cell end defining a distal inner angle in the expanded state, and a third inner cell edge attached to a fourth inner cell edge at a proximal inner cell end defining a proximal inner angle in the expanded state, the distal inner angle being distal the proximal inner angle along the longitudinal axis, wherein at least one outer perimeter is attached to at least one inner perimeter; and a plurality of tensioners having an extended length and a contracted length and comprising the second material, each inner cell having one tensioner being attached to the proximal inner cell end and extending distally to the distal inner cell end to apply a contraction force on the one inner cell.

2. The device of claim 1 wherein in each tensioner moves from the extended length to the contracted length to maintain a radial force on the vessel wall.

3. The device of claim 1 wherein the outer and inner perimeters are rhombic.

4. The device of claim 1 wherein the second and third outer cell edges form a first outer cell apex and the first and fourth outer cell edges form a second outer cell apex, and the second and third inner cell edges form a first inner cell apex and the first and fourth inner cell edges form a second inner cell apex.

5. The device of claim 4 wherein the first and second outer cell apices and the first and second inner cell apices are arcuate.

6. The device of claim 1 wherein the tensioner forms a first angle with the first inner cell edge and a second angle with the second inner cell edge, the sum of the first and second angles being about the same as the distal inner angle.

7. The device of claim 6 wherein the first and second angles are between about 25 to about 50 degrees in the expanded state.

8. The device of claim 1 wherein the inner layer, outer layer, and tensioners are a co-extrusion.

9. The device of claim 1 wherein the first material is a high mechanical strength material.

10. The device of claim 9 wherein the high mechanical strength material comprises at least one material selected from the group consisting of a polyurethane; a polyester; a polyanhydride; polylactide; poly-L-lactic acid; poly-L/D-latic acid; and a co-polymer of poly lactic-co-glycolic acid and polycaprolactone.

11. The device of claim 1 wherein the elastomeric material comprises polycaprolactone ranging from about 10 percent to about 100 percent of the elastomeric material.

12. The device of claim 1 wherein the first and second materials are biodegradable.

13. The device of claim 1 further comprising a plurality of filter struts attached to the inner layer.

14. The device of claim 13 wherein each filter strut comprises a proximal segment attached to the distal end and extending distally to a distal segment wherein all distal segments are attached to each other.

15. The device of claim 1 wherein the first outer and inner cell apices are each about 80 degrees to about 130 degrees in the expanded state and the second outer and inner cell apices are each about 80 degrees to about 130 degrees in the expanded state.

* * * * *

UNITED STATES PATENT AND TRADEMARK OFFICE
CERTIFICATE OF CORRECTION

PATENT NO. : 10,076,430 B2
APPLICATION NO. : 15/291384
DATED : September 18, 2018
INVENTOR(S) : Kasper Klausen Page 1 of 1

It is certified that error appears in the above-identified patent and that said Letters Patent is hereby corrected as shown below:

On the Title Page

Item (54), Title:
"Devce"
Should read:
"Device"

Signed and Sealed this
Twentieth Day of August, 2019

Andrei Iancu
*Director of the United States Patent and Trademark Office*